(12) United States Patent
Fan et al.

(10) Patent No.: US 11,331,654 B2
(45) Date of Patent: May 17, 2022

(54) CATALYST FOR AROMATIZATION OF LONG-CARBON CHAIN ALKANE AND PREPARATION METHOD AND USE THEREOF

(71) Applicant: Institute of Coal Chemistry, Chinese Academy of Sciences, Shanxi (CN)

(72) Inventors: Weibin Fan, Shanxi (CN); Jianguo Wang, Shanxi (CN); Mei Dong, Shanxi (CN); Qiuming Zhou, Shanxi (CN); Zhangfeng Qin, Shanxi (CN); Junten Li, Shanxi (CN)

(73) Assignee: Institute of Coal Chemistry, Chinese Academy of Sciences

( * ) Notice: Subject to any disclaimer, the term of this patent is extended or adjusted under 35 U.S.C. 154(b) by 78 days.

(21) Appl. No.: 16/882,573

(22) Filed: May 25, 2020

(65) Prior Publication Data
US 2021/0362138 A1   Nov. 25, 2021

(30) Foreign Application Priority Data

Apr. 9, 2019   (CN) .......................... 201910280378.4

(51) Int. Cl.
| | | |
|---|---|---|
| *C07C 5/367* | (2006.01) | |
| *B01J 29/44* | (2006.01) | |
| *B01J 37/30* | (2006.01) | |
| *B01J 37/02* | (2006.01) | |
| *B01J 37/10* | (2006.01) | |
| *C07C 6/10* | (2006.01) | |
| *C07C 5/32* | (2006.01) | |
| *C07C 4/00* | (2006.01) | |
| *C07C 6/08* | (2006.01) | |
| *C07C 5/393* | (2006.01) | |
| *C07C 5/41* | (2006.01) | |
| *C07C 13/271* | (2006.01) | |

(52) U.S. Cl.
CPC ........... *B01J 29/44* (2013.01); *B01J 37/0207* (2013.01); *B01J 37/10* (2013.01); *B01J 37/30* (2013.01); *C07C 4/00* (2013.01); *C07C 5/321* (2013.01); *C07C 5/322* (2013.01); *C07C 5/324* (2013.01); *C07C 5/325* (2013.01); *C07C 5/367* (2013.01); *C07C 5/393* (2013.01); *C07C 5/41* (2013.01); *C07C 5/412* (2013.01); *C07C 5/415* (2013.01); *C07C 5/417* (2013.01); *C07C 6/08* (2013.01); *C07C 6/10* (2013.01); *B01J 2229/42* (2013.01); *C07C 13/271* (2013.01); *C07C 2523/04* (2013.01); *C07C 2523/56* (2013.01); *C07C 2523/58* (2013.01); *C07C 2527/12* (2013.01); *C07C 2529/068* (2013.01); *C07C 2529/70* (2013.01)

(58) Field of Classification Search
CPC .... C07C 4/00; C07C 6/08; C07C 6/10; C07C 5/321; C07C 5/322; C07C 5/324; C07C 5/325; C07C 5/367; C07C 5/393; C07C 5/41; C07C 5/412; C07C 5/415; C07C 5/417; C07C 2523/04; C07C 2523/42; C07C 2523/56; C07C 2523/58; C07C 2527/12; C07C 2529/068; C07C 2529/70; C07C 2529/74
USPC ........ 585/407, 418, 419, 421; 208/133, 135, 208/137, 138, 139, 141
See application file for complete search history.

(56) References Cited

U.S. PATENT DOCUMENTS

| | | | | |
|---|---|---|---|---|
| 5,176,817 A | * | 1/1993 | Skeels .................... | C10G 11/05 208/108 |
| 5,366,616 A | * | 11/1994 | Skeels ...................... | B01J 29/04 208/106 |

* cited by examiner

*Primary Examiner* — Elizabeth D Wood
(74) *Attorney, Agent, or Firm* — Olive Law Group, PLLC (57) ABSTRACT

The present invention provides a catalyst for aromatization of a long-carbon chain alkane and a preparation method thereof. In the present invention, a molecular sieve containing a BEA structure is taken as an active component and mixed with a carrier, and then the mixture is formed, dried and calcined to obtain the catalyst for aromatization of a long-carbon chain alkane. The active component is prepared by taking a Naβ molecular sieve as a raw material and modifying through the following steps of: first obtaining an Hβ molecular sieve through ammonium ion-exchange, and then conducting dealumination and silicon insertion treatment of the Hβ molecular sieve through first hydrothermal treatment; forming a mesoporous structure in a molecular sieve framework through second hydrothermal treatment; reducing the acidity of the catalyst by potassium ion exchange, and finally using metal modification to improve the capability of the catalyst for catalyzing the aromatization of the long-carbon chain alkane and enhancing the toluene selectivity. The catalyst provided by the present invention shows high stability in the aromatization of the long-chain alkane and has a service life up to 170 h or above and aromatic hydrocarbon selectivity up to 80%, and the selectivity to toluene in aromatic hydrocarbon products can reach 85.5%.

2 Claims, 8 Drawing Sheets

CATALYST FOR AROMATIZATION OF LONG-CARBON CHAIN ALKANE AND PREPARATION METHOD AND USE THEREOF

CROSS REFERENCE TO RELATED APPLICATION

This application claims priority to Chinese Patent Application No. 201910280378.4, filed Apr. 9, 2019, the content of which is incorporated herein by reference in its entirety.

TECHNICAL FIELD

The present invention relates to the technical field of catalysts, and in particular, to a catalyst for aromatization of a long-carbon chain alkane and a preparation method and use thereof.

BACKGROUND

China promulgated the unleaded gasoline standard (GB17930-1999) in 2000. According to the standard, the volume content of olefin in gasoline shall be less than or equal to 35%, the volume content of benzene shall be less than or equal to 2.5%, the volume content of aromatic hydrocarbons shall be less than or equal to 40%, and the weight content of sulfur shall be less than or equal to 0.08%. China's gasoline mainly falls into FCC gasoline and coal-based catalytic synthetic oil. The FCC gasoline has relatively high sulfur and olefin contents. When a hydrodesulfurization process is used to reduce the content of sulfur in gasoline, some olefins will be converted to saturated alkanes, resulting in a decrease in octane number of the product. The coal-based catalytic synthetic oil also contains a large number of straight-chain alkanes, and hence, has a lower octane number. Aromatization of straight-chain alkanes in gasoline into aromatic hydrocarbons with a high octane number can improve the quality of gasoline. In addition, it can provide industrial raw materials such as benzene, toluene and xylene for organic chemical industry. Thus, it has attracted considerable research interests.

At present, aromatization of long-chain alkanes are mainly carried out on two kinds of catalysts. One is a platinum-loaded KL-type molecular sieve. L-type molecular sieve has a 12-membered ring (MR) straight pore structure with opening of 0.71 nm*0.71 nm. Such a pore structure is beneficial to the diffusion of reactants, but its one-dimensional feature causes coking easily, and consequently, resulting in the stability not high and the service life of the catalyst not long. In addition, the Pt/KL shows only high activity for aromatization of n-hexane (C6), while in the case of aromatization of C6+ or C6-alkane, the selectivity to aromatic hydrocarbon products is not higher. The other is metal-modified ZSM-5 catalysts. ZSM-5 has a three-dimensional pore architecture, but its ten-MR channels with medium pore openings is not conducive to the diffusion of long carbon-chain alkanes and their mixtures. In particular, ZSM-5 possesses strong acidity, and thus, often leads to formation of low contents about (40%) of aromatic hydrocarbon products but a large amount of dry gas byproducts. Patent No. CN1938245N discloses a Pt/Ga-ZSM-5 molecular sieve catalyst with MFI structure. It can be used for aromatization of C2-C6 alkanes, but shows poor catalytic activity for aromatization of long-chain alkanes. When catalyzing propane aromatization, it exhibits an aromatic hydrocarbon selectivity of about 30-40%.

U.S. Pat. No. 4,175,057 discloses a ZSM-5 molecular sieve catalyst loaded with Zn, Ga and Cu. This catalyst also shows an aromatic hydrocarbon selectivity of 30%-40% in the aromatization of propane and butane.

Patent No. CN1028729.1 invents an aromatization catalyst of a metal-modified ammonia ZSM-5 molecular sieve. It aims at aromatization of only C4-C6 alkanes, but the aromatic hydrocarbon yield can still reach only 45%.

Patent No. CN1070847A discloses an aluminum cross-linked smectite catalyst loaded with noble metal Pt or VII transition metal. This catalyst also shows an aromatic hydrocarbon selectivity of only 45.57% when catalyzing aromatization of C8-C9 alkanes.

Patent No. CN1830558A invents a ZSM-5 molecular sieve catalyst loaded with metal Zn and Ga. It can be used for aromatization of C3-C8 alkanes. For C6-C8 alkanes, the alkane conversion can reach 80.4% with aromatic hydrocarbon yield of about 80%, but its service life is only 9 h.

Patent No. CN1530426A discloses a hydrocarbon aromatization catalyst that is composed of metal Zn and/or Ga and a ZSM zeolite carrier with a Si/Al ratio of 20-300, where the metal elements are firstly loaded on the carrier by impregnation, and the metal dispersion, and thereby, the aromatization activity are improved by calcining in inert or reduction atmosphere. However, when catalyzing the aromatization of n-heptane, it gives the highest aromatic hydrocarbon yield of only 30%.

Patent No. CN102895992A issues an L-type molecular sieve catalyst for aromatization of alkanes, where the shaped L-type zeolite is prepared by in-situ crystallization, followed by loading metal Pt by impregnation. This catalyst shows an aromatic hydrocarbon yield of about 47% in the aromatization of n-heptane.

Patent No. CN1312736A discloses an L-type zeolite catalyst containing platinum, halogen and group IB metals. It gives an aromatic hydrocarbon yield of 64% with 37.1% of toluene in the aromatization of n-octane.

In the prior art, the catalysts applied for alkane aromatization are mostly MFI-type and L-type molecular sieves catalysts. β molecular sieve catalysts are rarely used to catalyze alkane aromatization. Patent No. CN107497475A discloses a molecular sieve catalyst loaded with metals. This patent only says that the molecular sieve can be a β molecular sieve, and does not report any catalytic results of β molecular sieves in catalyzing alkane aromatization in its examples. Document *Aromatization of n-Heptane on Pt/Alkali or Alkali-Earth Exchanged Beta Zeolite Catalysts: Catalyst Deactivation and Regeneration* published by F. J. Maldonado-Ho'dar et al. reports a Pt/Kβ molecular sieve catalyst. When the catalyst was used to catalyze the aromatization of n-heptane, the n-heptane conversion could get to 88.7% when the reaction was carried out for 7 min, but it deactivated at 40 min due to occurrence of significant coking; the n-heptane conversion rate was decreased to 60%. A further increase in the reaction time to 150 min led to a reduction of the n-heptane conversion to 54.7%, showing that the service life of the Pt/Kβ molecular sieve catalyst is very short.

The above results show that most of disclosed aromatization catalysts are aimed at low-carbon alkanes, and show lower aromatic hydrocarbon conversion and shorter service lives. The development of a catalyst for aromatization of a long-chain alkane with high activity, high stability and high aromatic hydrocarbon selectivity is of great significance to the improvement of gasoline quality in industry.

SUMMARY

In view of this, the present invention provides a catalyst for aromatization of a long-carbon chain alkane and a preparation method and use thereof. The catalyst for aromatization of a long-carbon chain alkane according to the present invention has high activity and good stability, and when the catalyst is applied to catalyzing aromatization of the long-carbon chain alkane, the aromatic hydrocarbon selectivity of the reaction is high.

To achieve the above purpose, the present invention provides the following technical solutions:

The present invention provides a method for preparing a catalyst for aromatization of a long-carbon chain alkane, where an active component of the catalyst is a β molecular sieve that has a BEA topological structure and is modified at a later stage, and the preparation method includes the following steps:

step (1): sequentially subjecting a Naβ molecular sieve to ammonium ion-exchange and first calcination to obtain an Hβ molecular sieve;

step (2): subjecting the Hβ molecular sieve to first hydrothermal treatment in an ammonium fluorosilicate aqueous solution and then second calcination; and subjecting the obtained product to second hydrothermal treatment in an alkaline salt solution to obtain a modified Hβ molecular sieve, where the alkaline salt includes a carbonate, a bicarbonate and/or and an alkali;

step (3): sequentially subjecting the modified Hβ molecular sieve to potassium ion-exchange and third calcination to obtain a modified Kβ molecular sieve;

step (4): impregnating the modified Kβ molecular sieve with a platinum-containing solution and then conducting fourth calcination to obtain a modified Pt/Kβ molecular sieve; and step (5): taking the modified Pt/Kβ molecular sieve as an active component, mixing with an inorganic oxide carrier, and then sequentially forming a uniform mixture, drying and calcining the mixture to obtain the catalyst for aromatization of a long-carbon chain alkane.

Preferably, an exchange solution for the ammonium ion-exchange in step (1) is an ammonium salt solution with a concentration of 0.1-1 mol/L;

the ammonium ion-exchange is conducted 1-4 times with a liquid to solid ratio of (10-60) mL:1 g at 50° C.-80° C. for 2-36 h; and in step (1), the first calcination is conducted at 450° C.-600° C. for 4-12 h.

Preferably, the concentration of the ammonium fluorosilicate aqueous solution in step (2) is 0.5-3 mol/L;

the first hydrothermal treatment is conducted at 50° C.-100° C. for 2-4h; and the second calcination is conducted at 450° C.-600° C. for 4-14 h.

Preferably, the concentration of the alkaline salt solution in step (2) is 0.5-3 mol/L; and the second hydrothermal treatment is conducted at 50° C.-100° C. for 2-4 h.

Preferably, an exchange solution for the potassium ion-exchange in step (3) is a potassium salt solution with a concentration of 1-5 mol/L; and the ammonium ion-exchange is conducted 2-4 times with a liquid to solid ratio of 20-70 mL:1 g at 50° C.-80° C. for 2-8 h.

Preferably, in step (3), the third calcination is conducted at 450° C.-600° C. for 4-14 h. Preferably, the platinum-containing solution in step (4) is a tetraammineplatinum chloride solution or a chloroplatinic acid solution;

when the tetraammineplatinum chloride solution is used, the fourth calcination is conducted at 250° C.-500° C. for 3-10 h; and when the chloroplatinic acid solution is used, the fourth calcination is conducted at 400° C.-450° C. for 3-10 h.

Preferably, the weight content of the modified Pt/Kβ molecular sieve in the catalyst for aromatization of a long-carbon chain alkane is 30%-70%, and the weight content of the inorganic oxide carrier on an oxide basis is 1%-40%.

Preferably, a precursor of the inorganic oxide carrier in step (5) is one or more of SB powder, dry glue powder, alumina sol, kaolin and pseudo-boehmite.

The present invention further provides a catalyst for aromatization of a long-carbon chain alkane prepared by the above preparation method, including an inorganic oxide carrier and a modified Pt/Kβ molecular sieve, where the modified Pt/Kβ molecular sieve includes a modified Kβ molecular sieve and a platinum oxide loaded on the modified Kβ molecular sieve; and based on the weight of metallic platinum, the loading amount of the platinum oxide on the modified Kβ molecular sieve is 1%-3%.

The present invention further provides use of the above catalyst for aromatization of a long-carbon chain alkane in catalyzing aromatization of the long-carbon chain alkane, where during use, the catalyst for aromatization of a long-carbon chain alkane is pretreated in a hydrogen atmosphere to reduce a platinum oxide to metallic platinum; and the long-carbon chain alkane is one or more of C5-C11 alkanes.

Preferably, the aromatization temperature of the long-carbon chain alkane is 400° C.-600° C.; the weight hourly space velocity (WHSV) of the long-carbon chain alkane in the aromatization of the long-carbon chain alkane is 0.5-5 $h^{-1}$, and the molar ratio of hydrogen to the long-carbon chain alkane is (4-10):1; and the catalyst for aromatization of a long-carbon chain alkane is pretreated in the hydrogen atmosphere for 5-10 h.

The present invention provides the method for preparing a catalyst for aromatization of a long-carbon chain alkane. An active component of the catalyst is a β molecular sieve that has a BEA topological structure and is modified at a later stage. The present invention is modified on the basis of the β molecular sieve, taking into account that the β molecular sieve is the only industrialized high-silica molecular sieve with a three-dimensional 12-MR channel, and has a pore size {[100] 0.66×0.67 nm<->[001] 0.56×0.56 nm} similar to that of the L-type molecular sieve, which theoretically has the advantages of not only facilitating the diffusion of reaction raw materials but also significantly alleviating coking process. However, the hydrothermal synthesized β molecular sieve generally has a silicon to aluminum atomic ratio of 12-30, and hence, has strong acidity. Therefore, in the present invention, later-stage modification of the parent β molecular sieve is conducted to improve its catalytic performance.

The present invention takes a Naβ molecular sieve as a raw material or a parent sample, and an Hβ molecular sieve is obtained through ammonium ion-exchange and calcination, thus ensuring the catalytic activity of the catalyst. In the present invention, dealumination and silicon insertion treatment of the catalyst are carried out using an ammonium fluorosilicate aqueous solution, thereby decreasing the strong acidity of the catalyst and avoiding the occurrence of side reactions. In addition, one-dimensional pore-structured molecular sieve is easily affected by diffusion resistance in the reaction process, thus decreasing the catalytic stability of the catalyst. In the present invention, alkali leaching treatment of the catalyst is conducted using a potassium carbonate aqueous solution with weak alkalinity or a low-concentration alkali solution, which can not only ensure the unique pore structure of the β molecular sieve but also make the β molecular sieve have hierarchical pores, thereby reducing the influence of diffusion resistance on the aromatization, alleviating the coking process, and greatly improving the catalytic stability or the service life of the catalyst. Finally, in the present invention, the catalytic ability of the catalyst for aromatization of long-carbon chain alkane is improved through metal modification, and the toluene selectivity is increased. The present invention provides a catalyst for aromatization of a long-carbon chain alkane, which is obtained by uniformly mixing and calcining an inorganic oxide carrier and a modified Pt/Kβ molecular sieve. The catalyst provided by the present invention is a metal-modified β molecular sieve, and shows high catalytic activity, high aromatics selectivity and long service life in the aromatization of long-carbon chain alkanes. Results of the examples show that the catalyst provided by the present invention has a service life of longer than 170 h, and a toluene selectivity of 85.5% in the aromatization of long-carbon chain alkanes.

DETAILED DESCRIPTION

The present invention provides a method for preparing a catalyst for aromatization of a long-carbon chain alkane. An active component of the catalyst is a β molecular sieve that has a BEA topological structure and is modified at a later stage. The preparation method includes the following steps:

step (1): sequentially subjecting a Naβ molecular sieve to ammonium ion-exchange and first calcination to obtain an Hβ molecular sieve;

step (2): subjecting the Hβ molecular sieve to first hydrothermal treatment in an ammonium fluorosilicate aqueous solution and then second calcination; and subjecting the obtained product to second hydrothermal treatment in an alkaline salt solution to obtain a modified Hβ molecular sieve, where the alkaline salt is a carbonate, a bicarbonate and/or and an alkali;

step (3): sequentially subjecting the modified Hβ molecular sieve to potassium ion-exchange and third calcination to obtain a modified Kβ molecular sieve;

step (4): impregnating the modified Kβ molecular sieve with a platinum-containing solution and then conducting fourth calcination to obtain a modified Pt/Kβ molecular sieve; and step (5): taking the modified Pt/Kβ molecular sieve as an active component, mixing with an inorganic oxide carrier, and then sequentially forming a uniform mixture, drying and calcining the mixture to obtain the catalyst for aromatization of a long-carbon chain alkane.

In the present invention, the Naβ molecular sieve is sequentially subjected to ammonium ion-exchange and first calcination to obtain an Hβ molecular sieve. In the present invention, the Si/Al ratio of the Naβ molecular sieve is preferably 10-50, more preferably 40. The present invention has no special requirements on the source of the Naβ molecular sieve, and a Naβ molecular sieve. It is commercially obtained or prepared by oneself.

In the present invention, when the Naβ molecular sieve is prepared by oneself, the preparation method preferably includes the following steps of:

mixing raw materials at a gel molar composition ratio of $SiO_2$:(0.01-0.04) $Al_2O_3$:(0.01-0.05) $Na_2O$:0.35 TEAOH:10 $H_2O$ to obtain initial gel;

subjecting the initial gel to hydrothermal reaction of to obtain a hydrothermal reaction product; and calcining the hydrothermal reaction product to obtain the Naβ molecular sieve.

In the present invention, the raw materials are preferably mixed at a gel molar composition ratio of $SiO_2$:(0.01-0.04) $Al_2O_3$:(0.01-0.05) $Na_2O$:0.35 TEAOH:10 $H_2O$ to obtain initial gel, more preferably at a ratio of $SiO_2$:0.03 $Al_2O_3$: (0.02-0.04) $Na_2O$:0.35 TEAOH:10 $H_2O$. The present invention has no special requirements on the types of the raw materials, and the initial gel with the above composition can be prepared by using the raw materials conventional to those skilled in the art.

In the present invention, the initial gel is preferably aged before crystallization. The aging time is preferably 2-4 h, more preferably 3 h. The present invention stabilizes a gel system through aging.

In the present invention, after completion of aging, the aged gel is preferably subjected to hydrothermal reaction to obtain a hydrothermal reaction product. In the present invention, the hydrothermal reaction is conducted at preferably 110° C.-170° C., more preferably 170° C.; and the hydrothermal reaction is conducted for preferably 70-80 h, more preferably 72 h.

In the present invention, after completion of the hydrothermal reaction, the solid product is separated from mother liquor by e.g. centrifugation and dried to obtain the hydrothermal reaction product. The present invention has no special requirements on the specific conditions of the centrifugation and drying, providing that the dried hydrothermal reaction product can be obtained.

In the present invention, after being obtained, the hydrothermal product is preferably calcined to obtain the Naβ molecular sieve. In the present invention, the calcination is conducted at preferably 500-600° C., more preferably 600° C.; and the calcination is conducted for preferably 7-9 h, more preferably 8 h.

In the present invention, after being obtained, the Naβ molecular sieve is sequentially subjected to ammonium ion-exchange and first calcination to obtain the Hβ molecular sieve. In the present invention, the ammonium ion-exchange solution is preferably an ammonium salt solution, more preferably an ammonium nitrate solution with a concentration of preferably 0.1-1 mol/L, more preferably 0.3-0.6 mol/L; the ammonium ion-exchange is conducted with a liquid to solid ratio of preferably (10-60) mL:1 g, more preferably (20-50) mL:1 g, the exchange times are preferably 1-4 times, more preferably 3 times, and the exchange temperature is preferably 50° C.-80° C., more preferably 60° C.-70° C.; the total time of the ammonium ion-exchange is preferably 2-36 h, more preferably 24-36 h; and the single ammonium ion-exchange is conducted for preferably 12-18 h, more preferably 14-16 h. In the present invention, Na+ ions in the Naβ molecular sieve are replaced with ammonium ion-exchange.

In the present invention, after the single ammonium ion-exchange is completed, an ammonium ion-exchange product is preferably washed and dried, and the dried product is subjected to ammonium ion-exchange again. The present invention has no special requirements on the specific conditions of the washing and drying, as long as the ammonium ion-exchange product can be cleaned and completely dried.

In the present invention, after ammonium ion-exchange is conducted 1-4 times, the ammonium ion-exchanged product is preferably dried. In the present invention, the drying is conducted at preferably 80° C.-120° C., more preferably 100° C., and the drying is conducted for preferably 11-13 h, more preferably 12 h. In the drying process of the present invention, some ammonium ions are converted into gas and removed.

In the present invention, after drying, the dried product is subjected to first calcination. In the present invention, the first calcination is conducted at 450-600° C., more preferably 450-550° C.; and the first calcination is conducted for 4-12 h, more preferably 6-10 h. In the present invention, water not removed in the drying process is further removed in the first calcination, and residual ammonium ions are also converted into gas in the calcination process, so that the Hβ molecular sieve is obtained.

In the present invention, the obtained Hβ molecular sieve is sequentially subjected to the first hydrothermal treatment in the ammonium fluorosilicate aqueous solution and then subjected to the second calcination. In the present invention, the concentration of the ammonium fluorosilicate aqueous solution is preferably 0.5-3 mol/L, more preferably 2-3 mol/L; and a ratio of the volume of the ammonium fluorosilicate aqueous solution to the weight of the Hβ molecular sieve is preferably (10-50) mL:1 g, more preferably 50 mL:1 g.

In the present invention, the first hydrothermal treatment is conducted at preferably 50-100° C., more preferably 50° C.; and the first hydrothermal treatment is conducted for preferably 2-4 h, more preferably 3 h. In the present invention, after ammonium fluorosilicate is hydrolyzed, hydrofluoric acid is generated. It can remove aluminum from a molecular sieve framework, and simultaneously, insert silicon atoms in the molecular sieve framework through isomorphous substitution, thereby increasing the Si/Al ratio of the framework and achieving the dealumination and silicon insertion, which reduces the acidity of the catalyst, and inhibits the generation of dry gas byproducts in n-heptane aromatization due to alleviation of cracking of long-carbon chain hydrocarbons.

In the present invention, the first hydrothermal treatment can play a role of dealumination and silicon insertion, and the number of times of the first hydrothermal treatment is preferably determined in terms of the Si/Al ratio required for the catalyst. In the specific example of the present invention, the number of times of the first hydrothermal treatment is preferably 2.

In the present invention, after completion of the first hydrothermal treatment, the solid product is separated from the hydrothermal treatment liquid by e.g. centrifugation, and dried. The drying is conducted at preferably 80° C.-120° C., more preferably 100° C.; and the drying is conducted for preferably 11-13 h, more preferably 12 h. In the present invention, the water unremoved in the drying process is completely removed by the second calcination.

In the present invention, after drying, the dried product is subjected to second calcination. In the present invention, the second calcination is conducted at preferably 450-600° C., more preferably 500-550° C.; and the second calcination is conducted for preferably 4-14 h, more preferably 6-12 h. In the present invention, water in the dried product is deeply removed by the second calcination.

In the present invention, after the second calcination is completed, the product having undergone the second calcination is subjected to second hydrothermal treatment in the alkaline salt solution to obtain the modified Hβ molecular sieve. In the present invention, the alkaline salt is a carbonate, a bicarbonate and/or and an alkali, more preferably potassium carbonate, sodium carbonate, potassium bicarbonate or sodium bicarbonate with a concentration of preferably 0.5-3 mol/L, more preferably 1-2 mol/L; the second hydrothermal treatment is conducted at preferably 50-100° C., more preferably 80° C.; and the second hydrothermal treatment is conducted at preferably 2-4 h, more preferably 3 h. In the present invention, the carbonate and the bicarbonate are weak acid salts. The hydroxide ions generated in their aqueous solutions leach part of the silicon atoms in the molecular sieve framework, leading to formation of a mesoporous structure. In the present invention, the alkali leaching causes the catalyst rich of mesopores, thus reducing the diffusion resistance of reactants and products, alleviating the deposition rate of carbon species and improving the catalytic stability and prolong the service life of the catalyst.

In the present invention, after the completion of the second hydrothermal treatment, the product is washed with water and dried to obtain the modified Hβ molecular sieve. The washing with water is to remove the residual alkaline solution in the hydrothermally treated product; the drying is conducted at preferably 80° C.-120° C., more preferably 100° C.; and the drying is conducted for preferably 11-13 h, more preferably 12 h.

In the present invention, after being obtained, the modified Hβ molecular sieve is sequentially subjected to potassium ion-exchange and third calcination to obtain the modified Kβ molecular sieve. In the present invention, an exchange solution for the potassium ion-exchange is preferably a potassium salt solution, more preferably a potassium nitrate solution with a concentration of preferably 1-5 mol/L, more preferably 3-5 mol/L; a liquid to solid ratio of the potassium ion-exchange is preferably (20-70) mL:1 g, more preferably (30-60) mL:1 g, the potassium ion-exchange times are preferably repeated 2-4 times, more preferably 3 times, and the potassium ion-exchange temperature is preferably 50° C.-80° C., more preferably 60° C.-70° C.; the total time of the potassium ion-exchange is preferably 2-8 h, more preferably 3-6 h; and the time of the single potassium ion-exchange is preferably 1-3 h, more preferably 2 h.

In the present invention, after the potassium ion-exchange is completed, the potassium ion-exchange product is preferably dried to obtain the modified Kβ molecular sieve. In the present invention, the drying is conducted at preferably 80° C.-120° C., more preferably 100° C.; and the drying is conducted for preferably 11-13 h, more preferably 12 h.

In the present invention, after being obtained, the modified Kβ molecular sieve is preferably impregnated in the platinum-containing solution and then subjected to fourth calcination to obtain the catalyst for aromatization of a long-carbon chain alkane. In the present invention, the platinum-containing solution is preferably a tetraammineplatinum chloride solution or a chloroplatinic acid solution with a concentration of preferably 0.1-1 mol/L, more preferably 0.3-0.6 mol/L; the impregnation time is preferably 6-24 h, more preferably 10-20 h; and in the present invention, the impregnation is preferably equal volume impregnation. In the impregnation process, platinum salt or platinate ions are loaded on the Kβ molecular sieve framework.

In the present invention, after the impregnation is completed, the impregnated product is dried; the present invention has no special requirements on the specific drying conditions, and drying conditions conventional to those skilled in the art can be used.

In the present invention, after being dried, the impregnated product is subjected to fourth calcination to obtain the modified Pt/Kβ molecular sieve. In the present invention, when the tetraammineplatinum chloride solution is used, the fourth calcination is conducted at preferably 250-500° C., more preferably 400-500° C., for preferably 3-10 h, more preferably 5-8 h; when the chloroplatinic acid solution is used, the fourth calcination is conducted at preferably 400-450° C., more preferably 450° C., for preferably 3-10 h, more preferably 3-5 h; and in the present invention, the fourth calcination is preferably conducted in an air atmosphere. In the calcination process, platinum salt or platinate is decomposed and oxidized in the air atmosphere to be loaded on the Kβ molecular sieve framework in the form of stable platinum oxide. When used, the catalyst for aromatization of a long-carbon chain alkane according to the present invention is pretreated in a hydrogen atmosphere to reduce the platinum oxide to metallic platinum with catalytic activity. In the present invention, the catalyst's capability of catalyzing aromatization of the long-carbon chain alkane is improved by metal platinum modification, and the toluene selectivity is improved.

In the present invention, after being obtained, the modified Pt/Kβ molecular sieve is taken as an active component and mixed with an inorganic oxide carrier, and then the mixture is sequentially formed, dried and calcined to obtain the catalyst for aromatization of a long-carbon chain alkane. In the present invention, the weight content of the modified Pt/Kβ molecular sieve in the catalyst for aromatization of a long-carbon chain alkane is preferably 30%-70%, more preferably 40%-60%, and the weight content of the inorganic oxide carrier on an oxide basis is preferably 1%-40%, more preferably 5%-30%; and a precursor of the inorganic oxide carrier is preferably one or more of SB powder, dry glue powder, alumina sol, kaolin and pseudo-boehmite.

The present invention has no special requirement for the specific conditions of the mixing, forming, drying and calcining, and conditions conventional to those skilled in the art can be used.

The present invention provides a catalyst for aromatization of long-carbon chain alkanes prepared by the above-described method. It is composed of an inorganic oxide carrier and a modified Pt/Kβ molecular sieve that is prepared by impregnating platinum oxide a modified Kβ molecular sieve and subsequently reduced in hydrogen atmosphere. In the present invention, based on the weight of metallic platinum, the loading amount of the platinum oxide on the modified Kβ molecular sieve is preferably 1%-3%, more preferably 2%-3%. This catalyst has high stability and shows high catalytic activity, high aromatic hydrocarbon selectivity and long service life in the aromatization of a long-chain alkane.

The present invention provides use of the catalyst for aromatization of a long-chain alkane, where during use, the catalyst is firstly pretreated in a hydrogen atmosphere to reduce the platinum oxide to metallic platinum; the long-chain alkane is one or more of C5-C11 alkanes, specifically one or more of C5-C11 straight-chain or branched-chain alkanes, and more specifically, for example, one or more of n-heptane, isoheptane, neoheptane, n-hexane, n-octane, isooctane, n-decane, etc. In the present invention, the aromatization temperature of the long-carbon chain alkane is preferably 400° C.-600° C., more preferably 450° C.-550° C.; the WHSV of the long-carbon chain alkane in the aromatization of the long-carbon chain alkane is preferably 0.5-5 $h^{-1}$, more preferably 1-4 $h^{-1}$; the molar ratio of hydrogen to the long-carbon chain alkane is preferably (4-10):1, more preferably (5-6):1; and the catalyst for aromatization of a long-carbon chain alkane is pretreated in the hydrogen atmosphere for preferably 5-10 h, more preferably 6-8 h before catalyzing the aromatization of a long-carbon chain alkane.

The catalyst for aromatization of a long-carbon chain alkane and the preparation method and use thereof provided by the present invention are described in detail below with reference to examples, but they cannot be understood as limiting the protection scope of the present invention.

Comparative Example 1

(1) Preparation of a Naβ Molecular Sieve 0.622 g of $NaAlO_2$ and 0.417 g of NaOH were sequentially added into 20.62 g TEAOH (25%) solution and stirred evenly until the solution was clear; Subsequently, 15.02 g of silica sol (JN40) was slowly added dropwise, and the solution was stirred and aged at room temperature for 4 h. and then sealed into a 100 mL high-pressure autoclave; hydrothermal reaction was carried out at 170° C. for 72 h. After that, the autoclave was taken out and cooled to room temperature with cool water. The sample was centrifuged, dried and calcined at 600° C. for 8 h to obtain a Naβ molecular sieve.

(2) Preparation of an Hβ Molecular Sieve 5 g of Naβ molecular sieve was added to 250 mL of $NH_4NO_3$ solution with a concentration of 1 mol/L, and stirred at 80° C. for 16 h to exchange Na+ ions with $NH_4^+$ cations. Then, it was centrifuged, washed with deionized water and dried. After being ion-exchanged twice according to the above procedures, the product was dried at 100° C. for 12 h, and then calcined at 500° C. for 6 h in air atmosphere in a muffle furnace to obtain an Hβ powdered molecular sieve; finally, the Hβ powdered molecular sieve was uniformly mixed with an inorganic oxide carrier, and the mixture was sequentially dried and calcined. The obtained sample, designated as 0 #, was tableted, crushed and sieved to 20-40 meshes for catalytic test.

(3) Preparation of a Pt/Kβ Molecular Sieve 2 g of Hβ molecular sieve prepared in step (1) was added to 100 mL of $KNO_3$ solution with a concentration of 4 mol/L and stirred at 80° C. for 2 h. Then, it was washed with deionized water and dried. After exchanging twice according to the above procedures, the molecular sieve was dried at 100° C. for 12 h and subsequently calcined in a muffle furnace at 550° C. for 6 h to obtain a Kβ powder molecular sieve.

1 g of kβ molecular sieve was loaded with 2% metal platinum by an equal volume impregnation method. The impregnation solution was a tetraammineplatinum chloride solution with a concentration of 0.0513 mol/L, and the molecular sieve was impregnated for 24 h; after that, it was dried and calcined at 400° C. for 6 h in a muffle furnace in air atmosphere to obtain a powder Pt/Kβ molecular sieve; then, the powder Pt/Kβ molecular sieve was uniformly mixed with an inorganic oxide carrier, and sequentially dried and calcined. The obtained sample, designated as catalyst 1 #, was pressed, crushed and sieved to 20-40 meshes for catalytic test.

Comparative Example 2

A NaL molecular sieve was used as a raw material, and processed according to steps (2) and (3) in Example 1 to obtain a Pt/KL molecular sieve. The powder Pt/KL molecular sieve was sequentially uniformly mixed with an inorganic oxide carrier, and dried and calcined. The obtained sample, denoted to catalyst 2 #, was pressed, crushed and sieved to 20-40 meshes for catalytic evaluation.

Comparative Example 3

A Na-ZSM-5 molecular sieve was used as a raw material, and processed according to steps (2) and (3) in Example 1 to obtain a Pt/KZSM-5 molecular sieve. The powder Pt/KZSM-5 molecular sieve was sequentially uniformly mixed with an inorganic oxide carrier, dried and calcined. The obtained sample, denoted to catalyst 3 #, was tableted, crushed and sieved to 20-40 meshes for catalytic test.

Example 1

(1) Preparation of an Hβ Catalyst Modified by Dealumination and Silicon Insertion An Hβ molecular sieve was prepared according to the method in Comparative Example 1. 50 mL of ammonium fluorosilicate solution with a concentration of 3 mol/L was slowly added dropwise to 1 g of Hβ molecular sieve with temperature controlled to 80° C. by a water bath and kept for 2 h; then the molecular sieve was washed with deionized water and dried. After being treated twice according to the above procedures, the product was dried at 100° C. for 12 h, and calcined at 550° C. for 6 h in air atmosphere in a muffle furnace to obtain a dealuminated and silicon-inserted Hβ molecular sieve; subsequently, it was sequentially uniformly mixed with an inorganic oxide carrier, dried and calcined. The obtained sample, designated as catalyst 4 #, was tableted, crushed and sieved to 20-40 meshes for catalytic evaluation.

(2) Preparation of an Alkali-Leached Mesoporous Hβ Molecular Sieve 1 g of dealuminated and silicon-inserted Hβ molecular sieve prepared in step (1) was added to 60 mL of $KCO_3$ solution with a concentration of 2 mol/L, stirred at 80° C. for 2 h; then, it was washed with deionized water and dried. After being dried at 100° C. for 12 h, the alkali-leached mesoporous Hβ molecular sieve was sequentially uniformly mixed with an inorganic oxide carrier, dried and calcined. The obtained sample, designated as catalyst 5 #, was pressed, crushed and sieved to 20-40 meshes for catalytic test.

(3) Preparation of a Modified Kβ Catalyst 2 g of alkali-leached mesoporous Hβ molecular sieve prepared in step (2) was added to 100 mL of $KNO_3$ solution with a concentration of 4 mol/L and kept at 80° C. for 2 h; then, it was washed with deionized water and dried. After being exchanged twice according to the above procedures, it was dried at 100° C. for 12 h and calcined at 550° C. for 6 h in air atmosphere in a muffle furnace; subsequently, it was sequentially uniformly mixed with an inorganic oxide carrier, dried and calcined. The obtained sample, designated as catalyst 6 #, was tableted, crushed and sieved to 20-40 meshes for catalytic test.

(4) Preparation of a Catalyst for Aromatization of Long-Carbon Chain Alkanes 1 g of modified kβ molecular sieve prepared in step (4) was loaded with 1% metallic platinum by an equal volume impregnation method. The impregnation solution was a tetraammineplatinum chloride solution with a concentration of 0.0513 mol/L, and the modified kβ molecular sieve was impregnated for 24 h, and subsequently dried and calcined at 400° C. for 6 h in air atmosphere in a muffle furnace to obtain a modified powder Pt/Kβ molecular sieve; the modified powder Pt/Kβ molecular sieve was used as an active component and mixed with an inorganic oxide carrier; then, the mixture was sequentially dried and calcined to obtain the catalyst of catalyst 7 #for aromatization of a long-chain alkane; before catalytic test, it was tableted, crushed and sieved to 20-40 meshes.

In the catalysts 1 #, 2 #, 3 #, 4 #, 5 #, 6 #and 7 #, the weight content of the active component was controlled to be 70%, and the weight content of the inorganic oxide on an oxide basis was controlled to be 10%, where the inorganic oxide was SB powder.

Pore Structure Test:

(1) Nitrogen Adsorption Test

Figure 1:
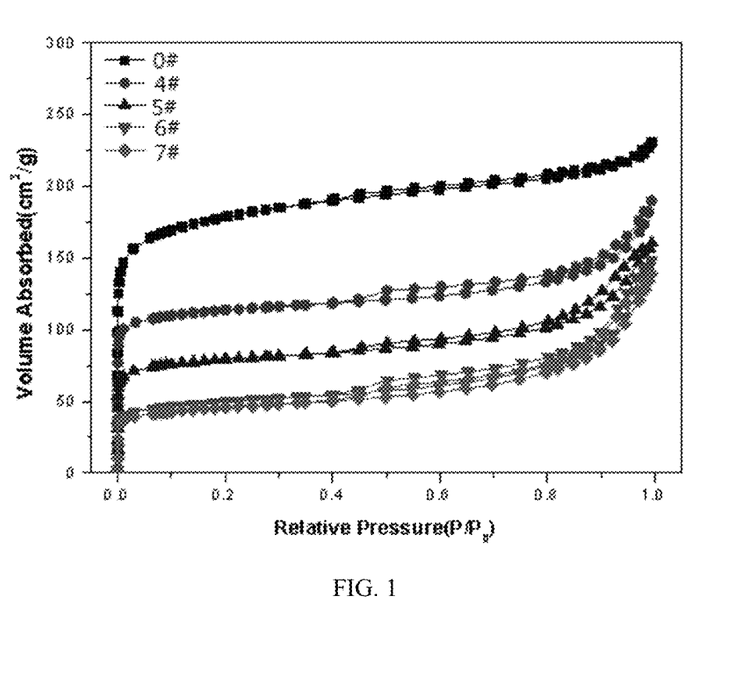
FIG. 1 is a diagram of nitrogen adsorption curves of catalysts 0 #, 4 #, 5 #, 6 #and 7 #according to examples of the present invention.

The Hβ molecular sieve catalyst (0 #) prepared in Comparative Example 1, the Hβ catalyst (4 #) modified by dealumination and silicon insertion prepared in Example 1, the alkali-leached mesoporous Hβ catalyst (5 #), the modified Kβ catalyst (6 #) and the catalyst (7 #) for aromatization of a long-chain alkane were subjected to a nitrogen adsorption test, and the obtained nitrogen adsorption curves are shown in FIG. 1. It can be seen that the catalysts 4 #, 5 #, 6 #and 7 #have obvious hysteresis loops in the $p/p^0$ range of 0.5-1.0, which is characteristic of H4-type pores, as classified by the International Union of Pure and Applied Chemistry (IUPAC), This indicates the existence of the irregular mesoporous structure, which is not present in the unmodified Hβ molecular sieve (1 #).

(2) Pore Diameter Distribution Test

Figure 2:
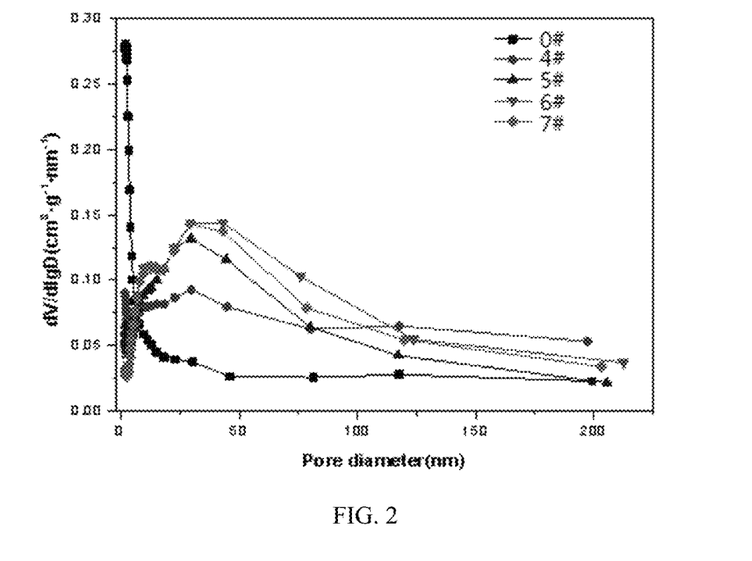
FIG. 2 is a diagram of pore diameter distribution curves of the catalysts 0 #, 4 #, 5 #, 6 #and 7 #according to examples of the present invention.

The Hβ molecular sieve catalyst (1 #) prepared in Comparative Example 1, the Hβ catalyst (4 #) modified by dealumination and silicon insertion in Example 1, the alkali-leaching mesoporous catalyst (5 #), the modified Kβ catalyst (6 #) and the catalyst (7 #) for aromatization of a long-chain alkane in Example 2 were subjected to a pore diameter distribution test, and the obtained pore diameter distribution curves are shown in FIG. 2. It can be seen that after a series of modifications, the formed catalyst (7 #) for aromatization of a long-chain alkane have mesopores with pore opening between 10 and 25 nm, and adsorption of a larger amount of $N_2$ and observation of more intense peak indicate the presence of more mesopores. The Hβ molecular sieve (1 #) without modification does not have mesopores.

The nitrogen adsorption result and the pore diameter distribution show that irregular mesoporous structures have formed in the Hβ molecular sieves modified by dealumination and silicon insertion, alkali leaching, and potassium ion exchange.

Application Examples 1-3

The catalyst is evaluated using a continuous flow fixed bed reactor, and the steps are as follows:

The aromatization of n-heptane was carried out in a continuous flow fixed bed microreactor loaded catalysts 1 #, 2 #and 3 #, respectively, under the following reaction conditions: atmospheric pressure, temperature of 480° C., time of 5 h, n-heptane WHSV of 1 $h^{-1}$, hydrogen to n-heptane molar ratio of 10. Before the reaction, the catalyst was pretreated at 480° C. for 4 h in hydrogen atmosphere. The collected products were analyzed by an Agilent 7890B gas chromatograph and an Agilent 7890A gas chromatograph.

Figure 3:
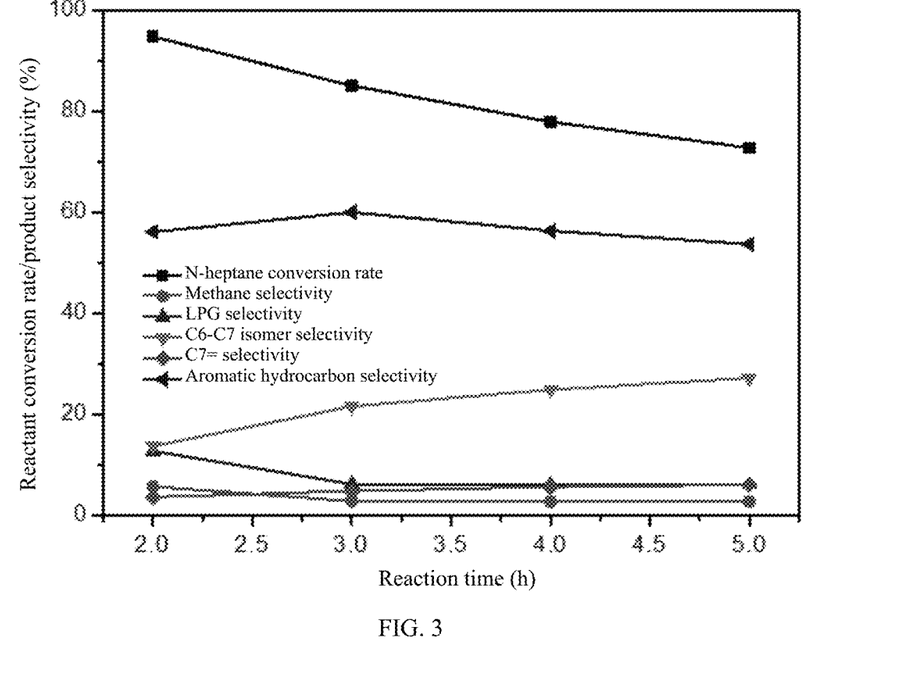
FIG. 3 shows catalytic result of the catalyst 1 #(Pt/Kβ molecular sieve) for n-heptane aromatization at 480° C.
Figure 4:
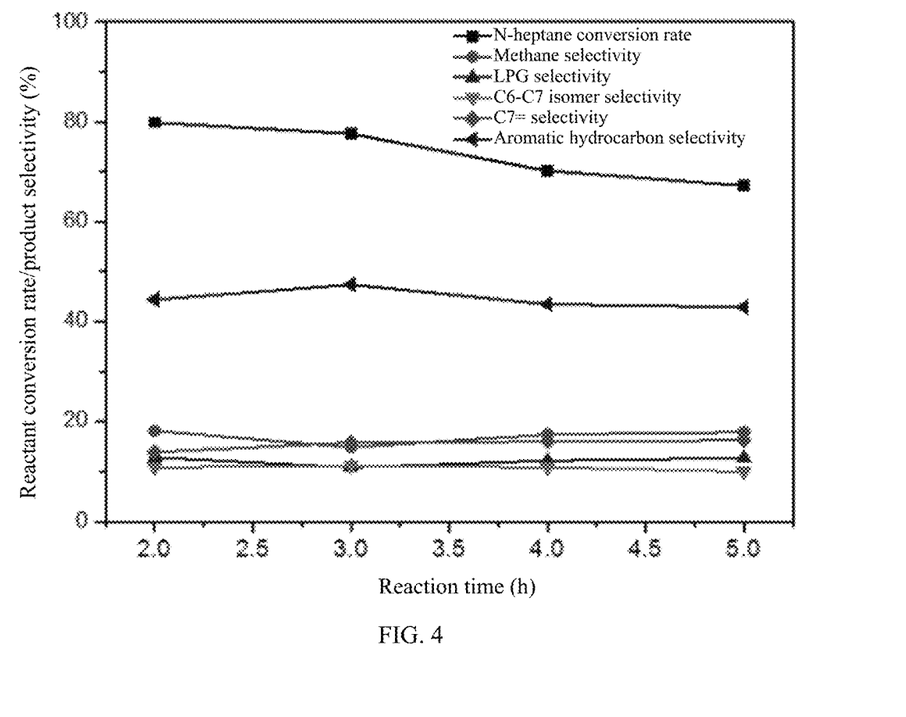
FIG. 4 shows the catalytic results obtained over the catalyst 2 #(Pt/KZSM-5 molecular sieve) catalysis in n-heptane aromatization at 480° C.
Figure 5:
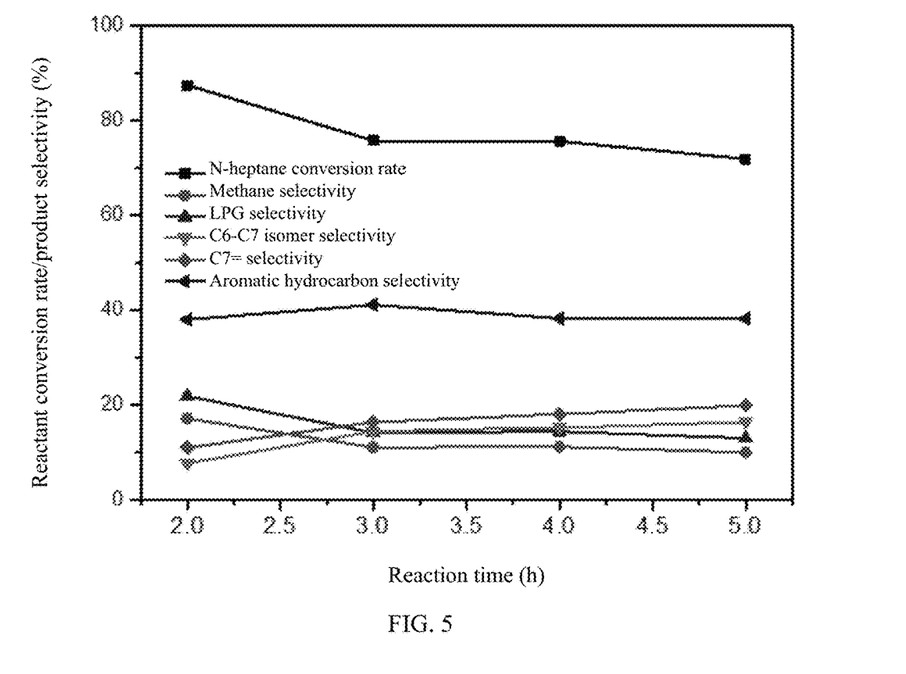
FIG. 5 shows catalytic results of the catalyst 3 #(Pt/KL molecular sieve) for n-heptane aromatization at 480° C.

The catalytic results of the catalysts 1 #, 2 #and 3 #for aromatization of n-heptane at 480° C. are shown in FIGS. 3, 4 and 5, respectively. The active components of the catalysts 1 #, 2 # and 3 # are Pt/Kβ, Pt/KL and Pt/KZSM-5 molecular sieves, respectively.

The reaction results of FIGS. 3-5 are compared in Table 1.

TABLE 1

Reactant conversions and product selectivity of Application Examples 1-3

| No. | Catalyst | n-Heptane conversion (%) | Aromatic hydrocarbon selectivity (%) | Methane selectivity (%) | LPG selectivity (%) | C6-C7 isomer selectivity (%) | C7⁻ selectivity (%) |
|---|---|---|---|---|---|---|---|
| Application Example 1 | Pt/Kβ (1#) | 72.8 | 53.7 | 2.8 | 6.2 | 27.2 | 6.2 |
| Application Example 2 | Pt/KL (2#) | 67.2 | 42.9 | 17.9 | 12.7 | 10.0 | 16.3 |
| Application Example 3 | Pt/KZSM-5 (3#) | 72.0 | 38.3 | 10.0 | 12.9 | 16.4 | 19.9 |

As can be seen from Table 1, the aromatic hydrocarbon selectivity is not high for all the three catalysts, where the catalyst 1 # shows the highest aromatic hydrocarbon selectivity of 53.7%.

Application Examples 4-6

The reaction conditions were the same as those employed in Application Examples 1-3 except that the reaction temperatures for n-heptane aromatization and corresponding hydrogen pretreatment were changed to 500° C., 550° C. and 600° C., respectively. The products were analyzed by an Agilent 7890B gas chromatograph and an Agilent 7890A gas chromatograph.

Figure 6:
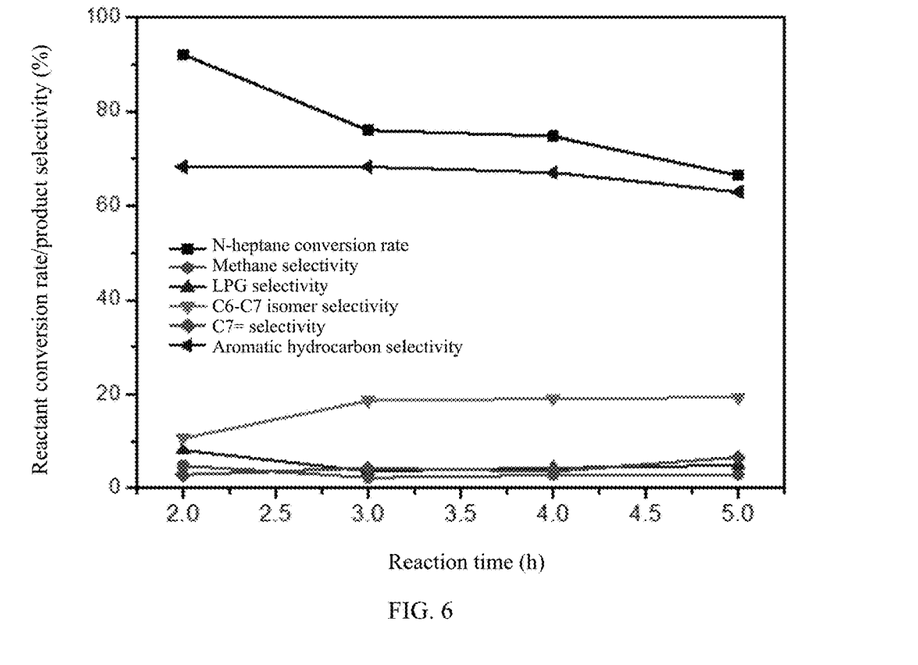
FIG. 6 shows the catalytic results of the catalyst 1 #(Pt/Kβ molecular sieve) for n-heptane aromatization at 500° C.
Figure 7:
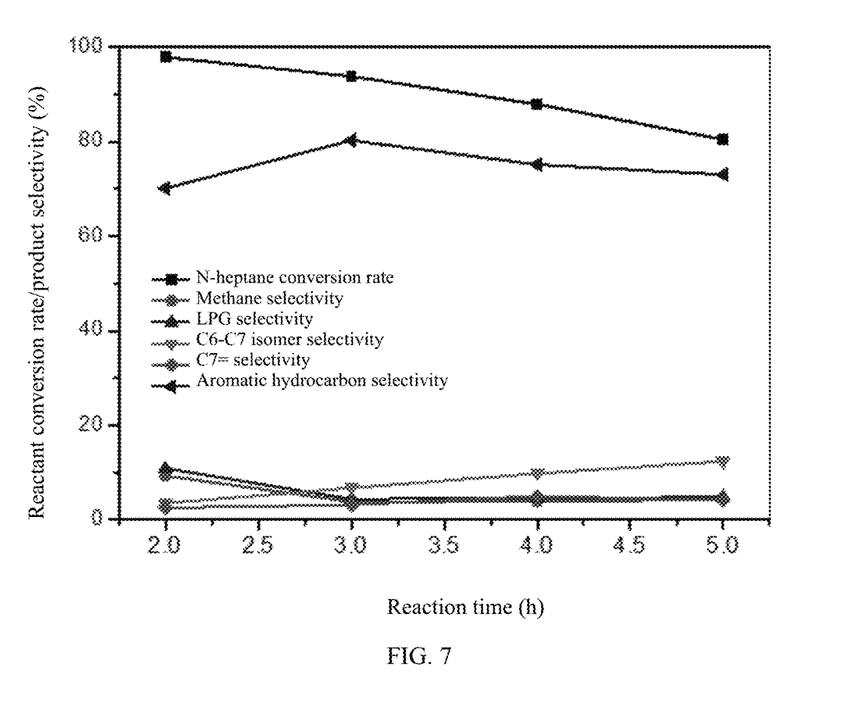
FIG. 7 shows the catalytic results obtained on the catalyst 1 #(Pt/Kβ molecular sieve) in n-heptane aromatization at 550° C.
Figure 8:
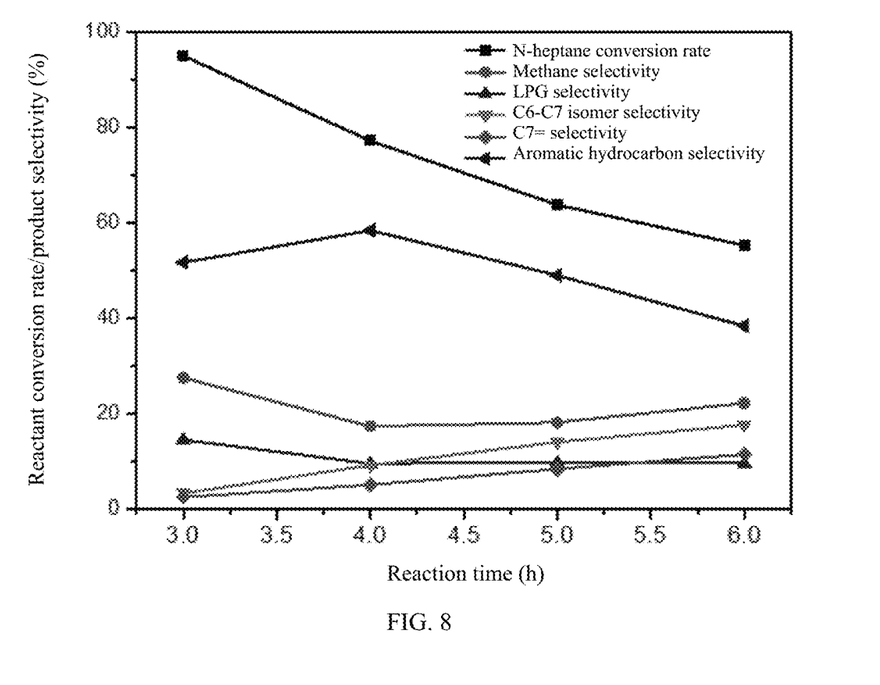
FIG. 8 shows the catalytic results of the catalyst 1 #(Pt/Kβ molecular sieve) for n-heptane aromatization at 600° C.

The reaction results are shown in FIGS. 6-8, where FIG. 6 shows the catalytic results of the catalyst 1 # (the active component is a Pt/Kβ molecular sieve) for n-heptane aromatization at 500° C.; FIG. 7 shows the results obtained in n-heptane aromatization over the catalyst 1 # (the active component is a Pt/Kβ molecular sieve) at 550° C.; and FIG. 8 shows the results obtained in n-heptane aromatization over the catalyst 1 # (the active component is a Pt/Kβ molecular sieve) at 600° C.

The reaction results of FIGS. 6-8 are compared in Table 2.

both 550° C.) except that the reaction was carried out on the catalyst 7 #. The products were analyzed by an Agilent 7890B gas chromatograph and an Agilent 7890A gas chromatograph.

Figure 9:
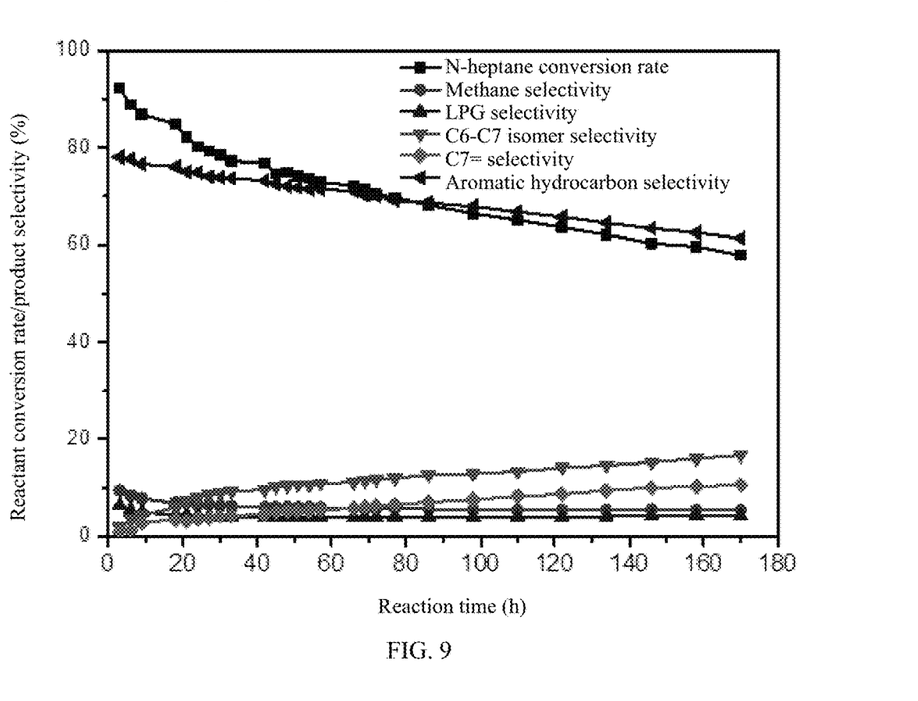
FIG. 9 shows the catalytic results obtained over the currently invented catalyst inn-heptane aromatization.
Figure 10:
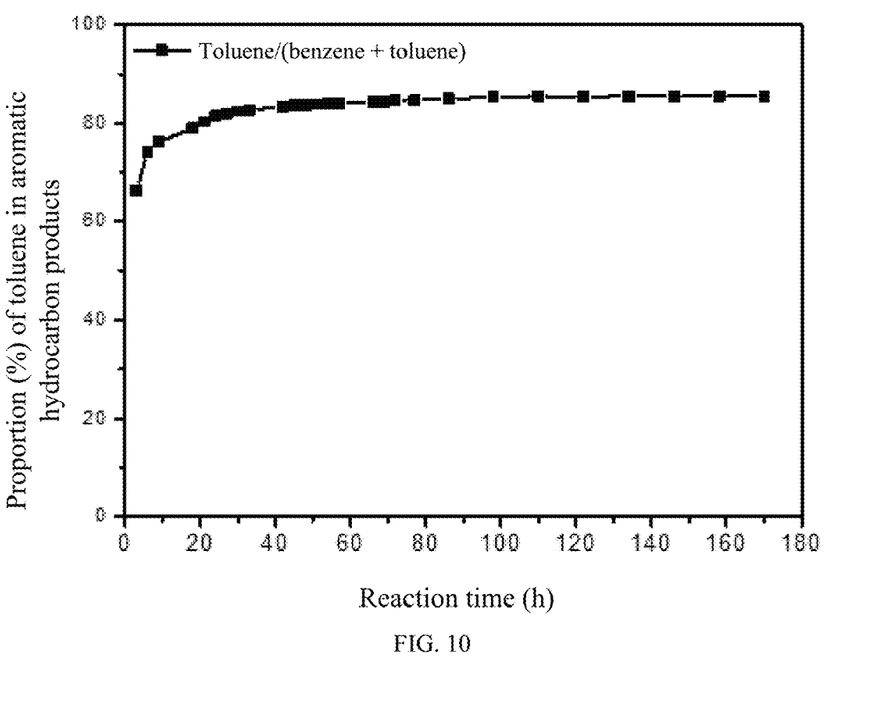
FIG. 10 shows the toluene selectivity in products obtained over the currently invented catalyst at different reaction time in n-heptane aromatization.

The reaction results are shown in FIGS. 9 and 10, where FIG. 9 shows the catalytic results of the catalyst 7 # for n-heptane aromatization; and FIG. 10 shows the evolution of toluene selectivity with the reaction time.

As can be seen from FIG. 9, when applied to n-heptane aromatization, the catalyst 7 # (the catalyst for aromatization of a long-chain alkane provided by the present invention) exhibits high catalytic stability and long catalytic life. It still possesses high catalytic activity after being used for 170 h or above, and the aromatic hydrocarbon selectivity reaches about 80% at the reaction time of 5 h.

As can be seen from FIG. 10, when applied to n-heptane aromatization, the catalyst 7 # (the catalyst for aromatization of a long-chain alkane provided by the present invention) shows high toluene selectivity, and the toluene selectivity in aromatic hydrocarbon products reaches 85.5% at stable stage.

Application Examples 8-13

The reaction conditions were the same as those in Application Example 5 (i.e., the reaction temperature and pretreatment temperature were 550° C.) except that reactants were changed to n-pentane, n-hexane, n-octane, n-nonane, n-decane and n-undecane respectively. The aromatization of

TABLE 2

Reactant conversions and product selectivity of Application Examples 4-6

| No. | Reaction temperature (° C.) | n-heptane conversion (%) | Aromatic hydrocarbon selectivity (%) | Methane selectivity (%) | LPG selectivity (%) | C6-C7 isomer selectivity (%) | C7⁻ selectivity (%) |
|---|---|---|---|---|---|---|---|
| Application Example 4 | 500 | 62.9 | 62.9 | 3.0 | 4.9 | 19.3 | 6.7 |
| Application Example 5 | 550 | 80.4 | 73.0 | 4.4 | 4.8 | 12.4 | 4.1 |
| Application Example 6 | 600 | 63.8 | 49.0 | 18.2 | 9.7 | 14.1 | 8.4 |

As can be seen from Table 1, the catalyst 1 # shows the highest aromatic hydrocarbon selectivity at 550° C., reaching 73%.

Application Example 7

The reaction conditions of n-heptane aromatization were the same as those in Application Example 5 (i.e., the reaction temperature and hydrogen pretreatment temperature were the forgoing alkanes was conducted on the catalyst 7 #, and the products were analyzed by an Agilent 7890B gas chromatograph and an Agilent 7890A gas chromatograph.

The catalytic results are shown in FIGS. 11-16.

Figure 11:
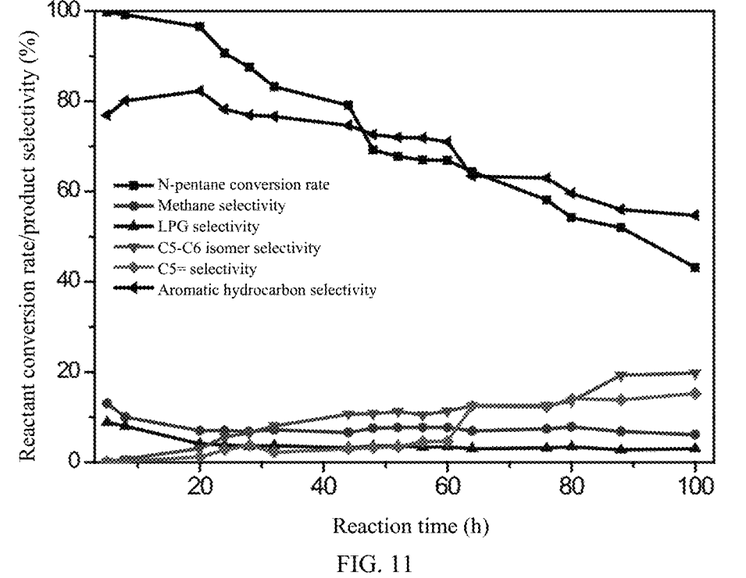
FIG. 11 shows the catalytic results of the currently invented catalyst for aromatization of n-pentane.

FIG. 11 shows the catalytic results for n-pentane aromatization on the catalyst 7 #. As can be seen from FIG. 11, when the catalyst 7 # provided by the present invention is applied to n-pentane aromatization, the service life can be 100 h or longer, and at the reaction time of 5 h, the aromatic hydrocarbon selectivity reaches about 80%.

Figure 12:
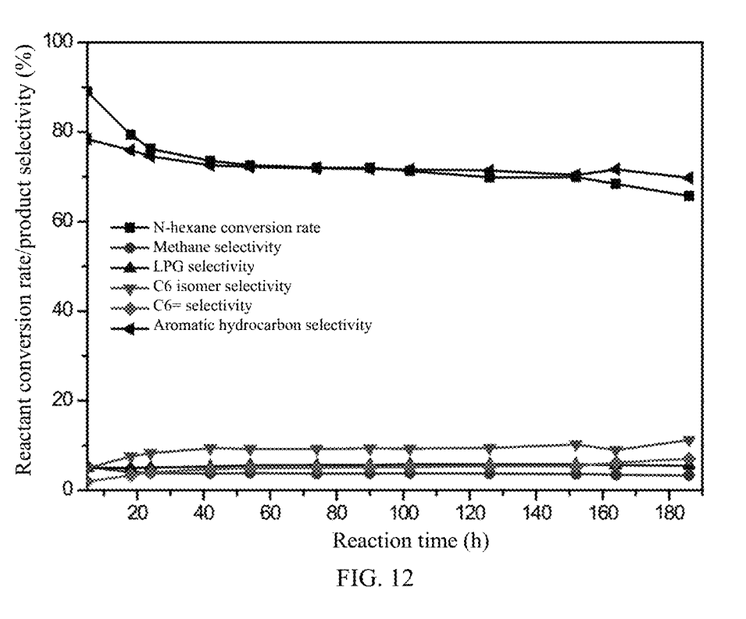
FIG. 12 shows the catalytic results of obtained over the currently invented catalyst in n-hexane aromatization.

FIG. 12 shows the reaction results obtained on the catalyst 7 #in n-hexane aromatization. As can be seen from FIG. 12, when applied to n-hexane aromatization, the catalyst 7 #provided by the present invention shows high stability and long catalytic life, and still high catalytic activity when the reaction is carried out for 180 h or longer. At the reaction time of 5 h, the aromatic hydrocarbon selectivity reaches about 80%.

Figure 13:
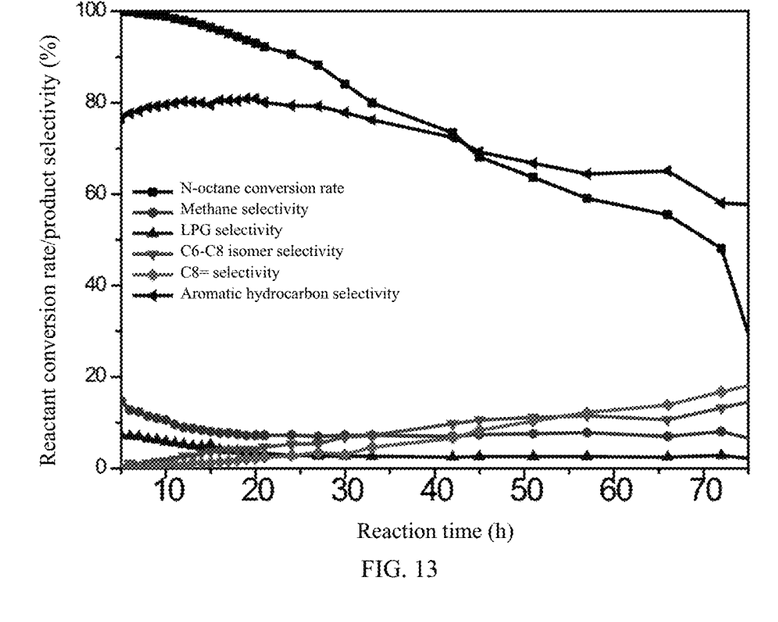
FIG. 13 shows the catalytic results of the currently invented catalyst for n-octane aromatization.

FIG. 13 shows the catalytic results of the catalyst 7 #for aromatization of n-octane. As can be seen from FIG. 13, when applied to n-octane aromatization, the catalyst 7 #provided by the present invention still shows high catalytic activity when the reaction time gets to 70 h or above, and the aromatic hydrocarbon selectivity reaches about 80% at the reaction time of 20 h.

Figure 14:
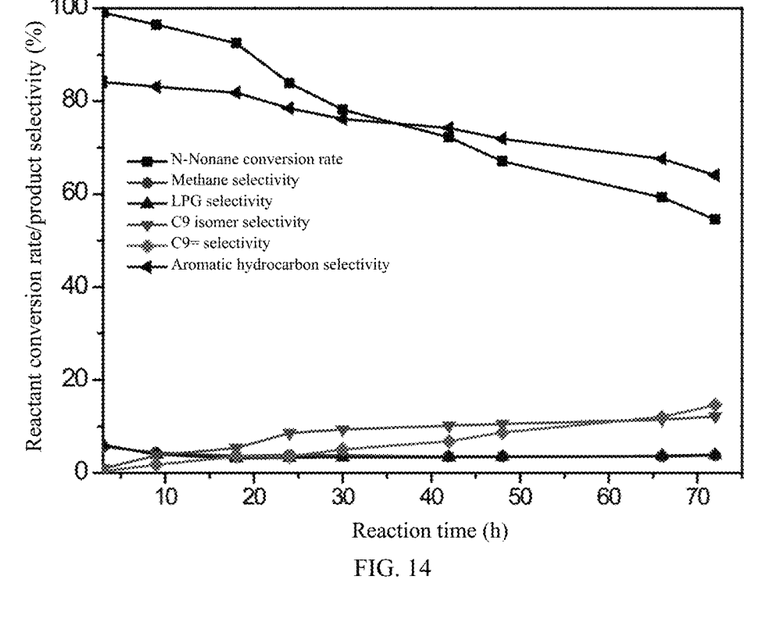
FIG. 14 shows the catalytic result for aromatization of n-nonane on the currently invented catalyst.

FIG. 14 shows the reaction results obtained on the catalyst 7 #in n-nonane aromatization. As can be seen from FIG. 14, when applied to n-Nonane aromatization, the catalyst 7 #provided by the present invention still shows high catalytic activity when the reaction is carried out for 70 h or longer, and the aromatic hydrocarbon selectivity reaches 80% or above at the reaction time of 5 h.

Figure 15:
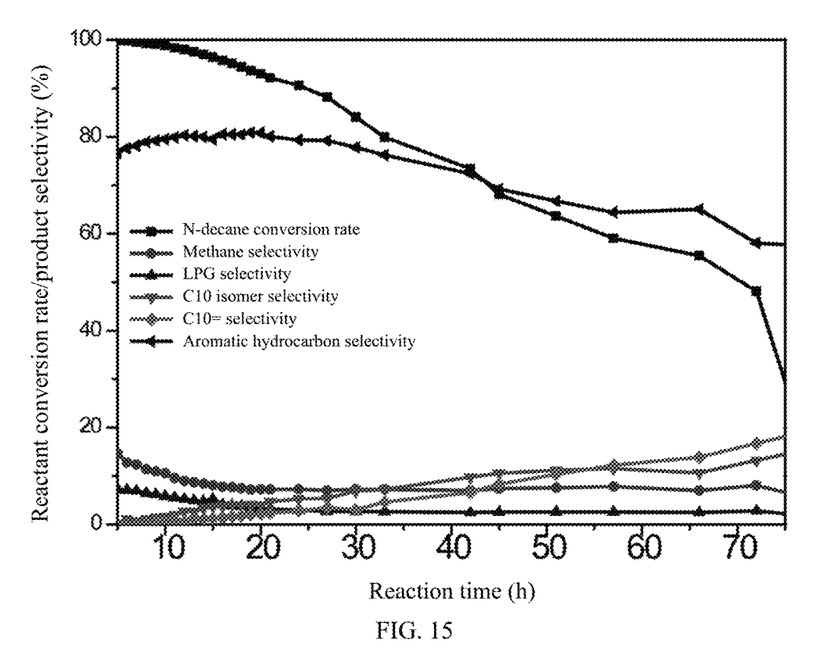
FIG. 15 shows the catalytic result for aromatization of n-decane on the currently invented catalyst.

FIG. 15 shows the catalytic results of the catalyst 7 #for aromatization of n-decane. As can be seen from FIG. 15, when the catalyst 7 #provided by the present invention is applied to n-decane aromatization, the service life is 70 h or longer, and at the reaction time of 5 h, the aromatic hydrocarbon selectivity reaches 80% or higher.

Figure 16:
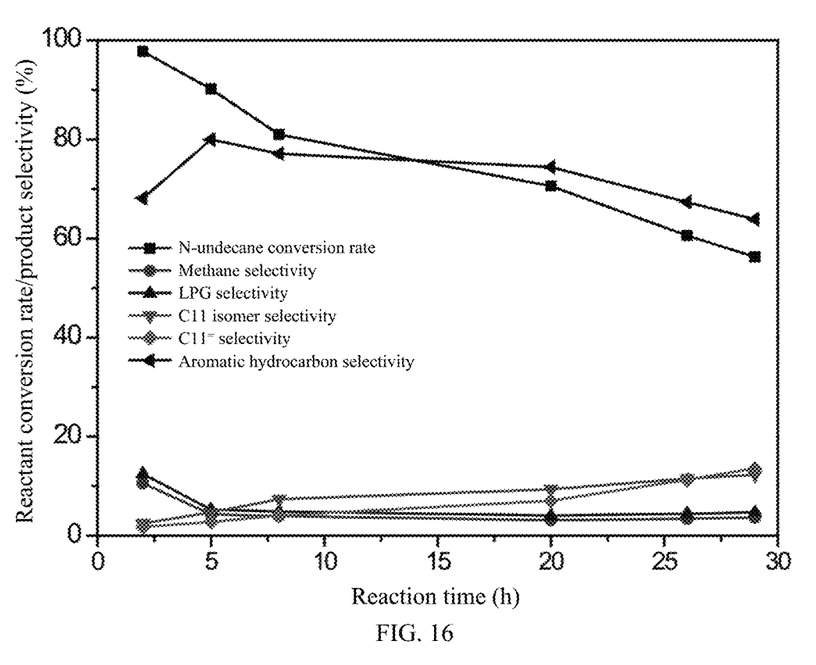
FIG. 16 shows the catalytic results of the currently invented catalysts for n-undecane aromatization.

FIG. 16 shows the reaction results obtained over the catalyst 7 #in n-undecane aromatization. As can be seen from FIG. 16, when applied to n-undecane aromatization, the catalyst 7 #provided by the present invention still exhibits high catalytic activity after reaction of 30 h or longer, and the aromatic hydrocarbon selectivity reaches about 80% at the reaction time of 5 h.

The above results indicate that the catalyst 7 #by the present invention can be used for catalyzing the aromatization of C5-C11 long-chain alkanes, and shows high catalytic activity, long service life and high aromatic hydrocarbon selectivity.

As can be seen from the above examples, the catalyst 7 #for aromatization of a long-chain alkane disclosed in the present invention has good stability, high catalytic activity and long service life, and when the catalyst 7 #is applied to catalyzing the aromatization of a long-chain alkane, the aromatic hydrocarbon selectivity is high, and the selectivity of toluene in aromatic hydrocarbon products is high.

The above descriptions are merely preferred implementations of the present invention. It should be noted that a person of ordinary skill in the art may further make several improvements and modifications without departing from the principle of the present invention, and such improvements and modifications shall also be deemed as falling within the protection scope of the present invention.

What is claimed is:

1. A method for using a catalyst for aromatization of a long-carbon chain alkane, comprising: pretreating the catalyst for aromatization of a long-carbon chain alkane in a hydrogen atmosphere to reduce a platinum oxide to metallic platinum; and contacting the long-carbon chain alkane with the pretreated catalyst for aromatization to generate an aromatic hydrocarbon;

wherein the long-carbon chain alkane is one or more of C5-C11 alkanes;

wherein the aromatization temperature is 400° C-600° C., the weight hourly space velocity (WHSV) in the aromatization of the long-carbon chain alkane is $0.5\text{-}5h^{-1}$, and the molar ratio of hydrogen to the long-carbon chain alkane is (4-10):1;

wherein the catalyst comprises an inorganic oxide carrier and a modified Pt/Kβ molecular sieve, wherein the modified Pt/Kβ molecular sieve comprises a modified Kβ molecular sieve and a platinum oxide loaded on the modified Kβ molecular sieve; and based on the weight of metallic platinum, the loading amount of the platinum oxide on the modified Kβ molecular sieve is 1%-3%;

wherein the method for modifying the catalyst for aromatization of a long-carbon chain alkane comprises the following steps:

step (1): sequentially subjecting a Naβ molecular sieve to ammonium ion-exchange and a first calcination to obtain an Hβ molecular sieve;

step (2): subjecting the Hβ molecular sieve to a first hydrothermal treatment in an ammonium fluorosilicate aqueous solution and then a second calcination; and subjecting the obtained product to a second hydrothermal treatment in an alkaline salt solution to obtain a modified Hβ molecular sieve, wherein the alkaline salt comprises a carbonate, a bicarbonate and/or and an alkali;

step (3): sequentially subjecting the modified Hβ molecular sieve to potassium ion-exchange and a third calcination to obtain a modified Kβ molecular sieve;

step (4): impregnating the modified Kβ molecular sieve with a platinum-containing solution and then conducting a fourth calcination to obtain a modified Pt/Kβ molecular sieve; and step (5): mixing the modified Pt/Kβ molecular sieve as an active component with an inorganic oxide carrier, and then sequentially forming a uniform mixture, drying and calcining the mixture to obtain the catalyst for aromatization of a long-carbon chain alkane.

2. The method according to claim 1, wherein the catalyst for aromatization of a long-carbon chain alkane is pretreated in the hydrogen atmosphere for 5-10 h.

* * * * *

UNITED STATES PATENT AND TRADEMARK OFFICE
CERTIFICATE OF CORRECTION

| | |
|---|---|
| PATENT NO. | : 11,331,654 B2 |
| APPLICATION NO. | : 16/882573 |
| DATED | : May 17, 2022 |
| INVENTOR(S) | : Weibin Fan et al. |

It is certified that error appears in the above-identified patent and that said Letters Patent is hereby corrected as shown below:

On the Title Page

Item [72], replace "Junten Li" with "Junfen Li".

Signed and Sealed this
Twenty-sixth Day of July, 2022

*Katherine Kelly Vidal*

Katherine Kelly Vidal
*Director of the United States Patent and Trademark Office*